United States Patent [19]

Inoue et al.

[11] Patent Number: 4,617,141
[45] Date of Patent: Oct. 14, 1986

[54] TRANS-4-ALKYLOXYMETHYL-1-(4'-SUBSTITUTED BIPHENYLYL-4)CYCLOHEXANES

[75] Inventors: Hiromichi Inoue; Takashi Inukai; Yasuyuki Goto; Hideo Sato; Masahiro Fukui, all of Kanagawaken, Japan

[73] Assignee: Chisso Corporation, Osaka, Japan

[21] Appl. No.: 712,752

[22] Filed: Mar. 18, 1985

Related U.S. Application Data

[62] Division of Ser. No. 502,233, Jun. 8, 1983, Pat. No. 4,522,741.

[30] Foreign Application Priority Data

Jun. 12, 1982 [JP] Japan ................................ 57-101172

[51] Int. Cl.⁴ ........................... C09K 3/34; G02F 1/13; C07C 43/168
[52] U.S. Cl. .............................. 252/299.63; 252/299.5; 252/299.67; 350/350 R; 350/350 S; 568/659; 568/664
[58] Field of Search ............ 252/299.5, 299.63, 299.67; 568/659, 664; 350/350 R, 350 S

[56] References Cited

U.S. PATENT DOCUMENTS

| | | | |
|---|---|---|---|
| 4,330,426 | 5/1982 | Eidenschink et al. | 252/299.63 |
| 4,331,552 | 5/1982 | Eidenschink et al. | 252/299.6 |
| 4,361,494 | 11/1982 | Osman et al. | 252/299.63 |
| 4,431,564 | 2/1984 | Fukui et al. | 252/299.66 |
| 4,452,719 | 6/1984 | Inoue et al. | 252/299.63 |
| 4,468,240 | 8/1984 | Inoue et al. | 252/299.63 |
| 4,477,369 | 10/1984 | Sugimori et al. | 252/299.63 |
| 4,507,222 | 3/1985 | Inoue et al. | 252/299.63 |
| 4,564,694 | 1/1986 | Hirai et al. | 252/299.63 |

FOREIGN PATENT DOCUMENTS

| | | | |
|---|---|---|---|
| 58981 | 9/1982 | European Pat. Off. | 252/299.63 |
| 90548 | 10/1983 | European Pat. Off. | 252/299.63 |
| 57-49688 | 3/1982 | Japan | 252/299.63 |
| 57-77658 | 5/1982 | Japan | 252/299.67 |
| 57-99542 | 6/1982 | Japan | 252/299.63 |
| 57-108056 | 7/1982 | Japan | 252/299.66 |
| 58-134046 | 8/1983 | Japan | 252/299.63 |

Primary Examiner—Teddy S. Gron
Attorney, Agent, or Firm—Wenderoth, Lind & Ponack

[57] ABSTRACT

Novel liquid crystal compounds having a higher clearing point and a superior stability are provided, which are trans-4-alkyloxymethyl-1-(4'-substituted biphenylyl-4)cyclohexanes expressed by the general formula (I):

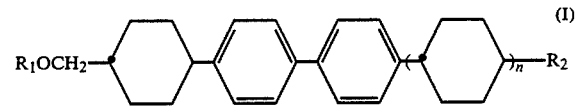

wherein $R_1$ and $R_2$ each represent an alkyl group of 1 to 8 cabon atoms and n represents 0 or 1.

3 Claims, No Drawings

TRANS-4-ALKYLOXYMETHYL-1-(4'-SUBSTITUTED BIPHENYLYL-4)CYCLOHEXANES

This application is a division of Ser. No. 502,233 filed June 8, 1983, U.S. Pat. No. 4,522,741.

BACKGROUND OF THE INVENTION

1. Field of the Invention

This invention relates to novel liquid crystal compounds and liquid crystal compositions containing the same.

2. Description of the Prior Art

Liquid crystal display elements utilize the optical anisotropy and dielectric anisotropy of liquid crystal substances and are classified into TN type (twisted nematic type), DS type (dynamic scattering type), guest-host type, DAP type, etc. according to their modes based on principle. Due to differences between these modes, the optimum characteristics of liquid crystal substances suitable to their respective uses are different. At any rate, however, it is common to these liquid crystal substances that they are required to be stable to moisture, air, heat, light, etc. Further, they are required to be capable of existing in the form of a liquid crystal phase at least in the range of 0° to 60° C. However, no single compound exists which satisfies all of these conditions, but it is the present status that mixtures of several kinds of liquid crystal compounds or nonliquid crystal compounds have been practically used as a liquid crystal composition.

SUMMARY OF THE INVENTION

The object of the present invention is to provide compounds which are useful as a component constituting liquid crystal compounds useful for TN display elements, and particularly effective for raising their N-I point (clearing point).

The compounds of the present invention are trans-4-alkyloxymethyl-1-(4'-substituted biphenylyl-4)cyclohexanes expressed by the following general formula (I):

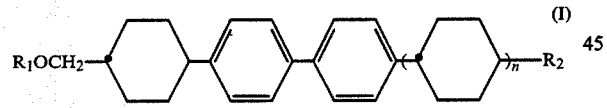

wherein $R_1$ and $R_2$ each represent an alkyl group of 1 to 8 carbon atoms, preferably 1 to 5 carbon atoms and n represents 0 or 1.

DETAILED DESCRIPTION OF PREFERRED EMBODIMENTS

The compounds of the present invention are novel liquid crystal compounds having a higher clearing point and a superior stability. These compounds cannot be singly applied for practical use, but due to their superior compatibility with other liquid crystal compounds, when they are admixed with one kind or a mixture of several kinds of liquid crystals of e.g. biphenyl group, ester group, azoxy group, cyclohexanecarboxylic acid ester group, phenylcyclohexane group, phenylpyrimidine group, phenylmetadioxane group, etc., they are effective for raising their clearing point. Moreover, when the compounds of the present invention are used, it is possible to extend the temperature range on the lower temperature side and thereby provide a liquid crystal composition having superior low temperature response characteristics.

Compounds of the formula (I) are prepared through the following steps:

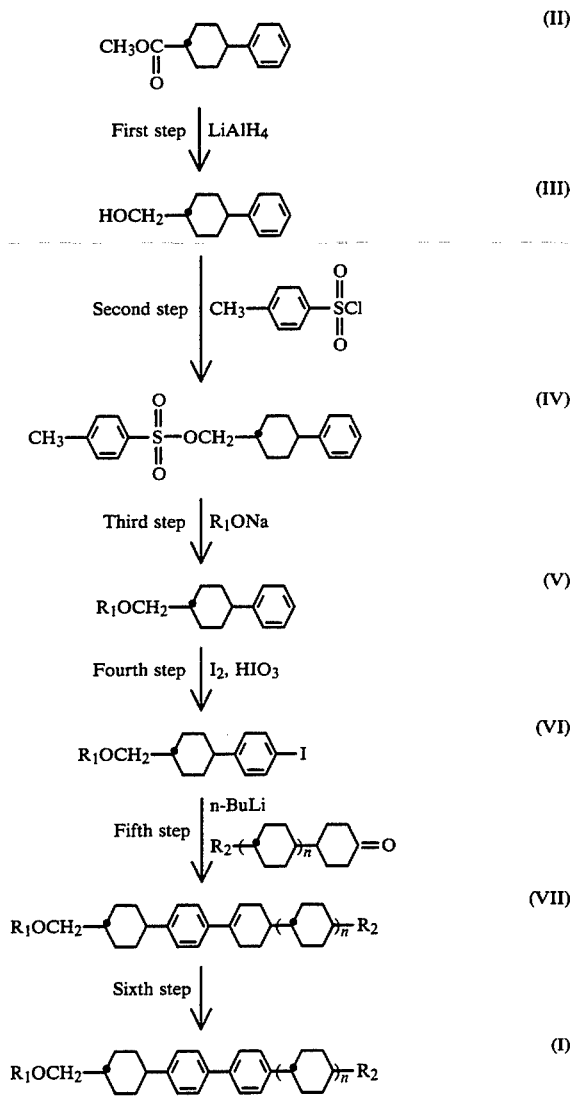

First, trans-4-phenylcyclohexanecarboxylic acid methyl ester (II) (W. S. Johnson et al, J.A.C.S., 67, 1045 (1945)) which is a known substance is reduced with a reducing agent such as lithium aluminum hydride (LiAlH$_4$) or according to a known reduction method to obtain trans-4-phenylcyclohexylmethanol (III), which is then reacted with p-toluenesulfonyl chloride in dry pyridine to obtain p-toluenesulfonic acid trans-4-phenylcyclohexyl methyl ester (IV), which is then reacted with an alcoholate to obtain a trans-4-alkyloxymethyl-1-phenylcyclohexane (V), which is then heated together with iodine and hydroiodic acid in a solvent such as N,N-dimethylformamide, dimethylsulfoxide, etc. to obtain a trans-4-alkyloxymethyl-1-(4'-iodophenyl)cyclohexane (VI), the iodine of which is then replaced by Li with a hexane solution of n-butyllithium (n—C$_4$H$_9$Li) to obtain a

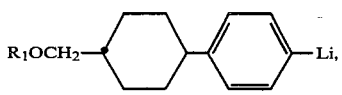

which is further reacted with a 4-substituted cyclohexanone to obtain a trans-4-alkyloxymethyl-1-(4'-substituted cyclohexenylphenyl)cyclohexane (VII) which is then heated together with a dehydrotreating agent in an inert organic solvent such as toluene, xylene, etc. to obtain a compound of the formula (I) of the present invention.

When, in the above third step, the compound (IV) is reacted with, as an alcoholate, sodium methoxide, sodium ethoxide, sodium propoxide, sodium butoxide, sodium pentoxide, sodium hexyloxide, sodium heptyl oxide, sodium octyloxide, respectively, and in the fifth step, there is used 4-methylcyclohexanone, 4-ethylcyclohexanone, 4-propylcyclohexanone, 4-butylcyclohexanone, 4-pentylcyclohexanone, 4-hexylcyclohexanone, 4-heptylcyclohexanone, 4-octylcyclohexanone, 4-(trans-4-methylcyclohexyl)cyclohexanone, 4-(trans-4-ethylcyclohexyl)cyclohexanone, 4-(trans-4-propylcyclohexyl)cyclohexanone, 4-(trans-4-butylcyclohexyl)cyclohexanone, 4-(trans-4-pentylcyclohexyl)cyclohexanone, 4-(trans-4-heptylcyclohexyl)cyclohexanone, or 4-(trans-4-octylcyclohexyl)cyclohexanone, then it is possible to prepare as final products, compounds of the formula (I) wherein $R_1$ and $R_2$ are each various kinds of alkyl groups.

Next, preparation, properties and use of the compounds of the present invention will be described in detail by way of Examples.

EXAMPLE 1

Preparation of trans-4-methyloxymethyl-1-(4'-propylbiphenylyl-4)cyclohexanone (a compound of the formula (I) wherein n=0, $R_1=CH_3$ and $R_2=C_3H_7$)

First Step

Dry tetrahydrofuran (THF) (420 ml) was added to lithium aluminum hydride (11.1 g, 0.293 mol), and while the mixture was vigorously agitated, there was dropwise added a solution obtained by dissolving trans-4-phenylcyclohexanecarboxylic acid methyl ester (II) (64.0 g, 0.293 mol) in THF (70 ml), at a reaction temperature kept at 20° C. or lower. After completion of the addition, the reaction mixture was warmed up to 55° C., followed by reacting it for 2 hours and cooling. Ethyl acetate (12 ml) and water (100 ml) were then added, followed by adding a 1N aqueous solution of sulfuric acid (350 ml) to dissolve inorganic matter, separating the resulting organic layer and aqueous layer from one another, adding n-heptane (200 ml) to extract the organic layer, washing the extract solution with water (500 ml), then washing with a 2% aqueous solution of $Na_2CO_3$, further washing with water until the aqueous layer became neutral, distilling off n-heptane and THF, recrystallizing the resulting solid as residue from n-heptane (20 ml), filtering off crystals and drying to obtain 4-phenylcyclohexylmethanol (III) (51.4 g). M.P. 47.3°~48.5° C.

Second Step

Compound (III) (50 g, 0.268 mol) was dissolved in dry pyridine (110 ml) and cooled to 5° C. or lower. To this solution was dropwise added a solution of p-toluenesulfonic chloride (50.1 g, 0.263 mol) dissolved in dry toluene (70 ml), through a dropping funnel in small portions so that the reaction temperature could not exceed 10° C. After completion of the addition, the cooling bath was removed and agitation was carried out at room temperature for 4 hours, followed by adding water (100 ml) and toluene (300 ml) to extract the resulting product, washing the toluene-extraction liquid twice with 6N-HCl (100 ml), then once with water (200 ml), further twice with 2N aqueous solution of NaOH (100 ml), and 4 times with water (200 ml), distilling off the solvent, recrystallizing the residue from toluene (90 ml), filtering off and drying to obtain p-toluenesulfonic acid trans-4-phenylcyclohexyl methyl ester (IV) (77.0 g). M.P. 108.0°~108.7° C.

Third step

Slices of metal Na (17.4 g, 0.755 mol) were added in small portions to methyl alcohol (250 ml) agitated at room temperature to prepare sodium methoxide. After metal Na pieces disappeared, a solution obtained by dissolving the compound (IV) (200.0 g, 0.581 mol) obtained above, in dry toluene (600 ml), was gradually added through a dropping funnel so that the inner temperature could keep within a range of 50° to 60° C. After completion of the addition, the mixture was refluxed for 4 hours, followed by cooling, adding water (20 ml), transferring into a separating funnel, washing the resulting toluene layer with water until the aqueous layer became neutral, distilling off toluene under reduced pressure, distilling under reduced pressure and collecting fractions of boiling points of 105°~108° C./1.5 mmHg to obtain trans-4-methyloxymethyl-1-phenylcyclohexane (V) (100.0 g).

Fourth step

Into a 1 l three-neck flask were added the compound (V) (100.0 g, 0.489 mol) obtained at the third step, acetic acid (344 ml), water (91 ml), hydroiodic acid (20.6 g, 0.117 mol), iodine (54.5 g, 0.215 mol), CCl$_4$ (40 ml), and conc. hydrochloric acid (14 ml), followed by stirring, heating under reflux for 3 hours for reaction, cooling, adding a 10% aqueous solution of sodium thiosulfate (15 ml), reducing excess iodine, adding n-heptane (200 ml) to extract the resulting product, washing n-heptane layer with water until the aqueous layer became neutral, distilling off n-heptane under reduced pressure, dissolving the residue in n-hexane (50 ml), allowing the solution to stand at −10° to −20° C. for 12 hours, filtering off the resulting crystals and drying to obtain 4-(trans-4'-methyloxymethylcyclohexyl)iodobenzene (VI) (81.3 g). M.P. 40.3°~42.3° C.

Fifth step

Into a 500 ml three-neck flask were placed the compound (VI) (21 g, 0.064 mol) obtained at the fourth step and dry toluene (40 ml) in dry nitrogen atmosphere, followed by dissolving with stirring. To the solution was dropwise added a commercially available 1.67N hexane solution (42.7 ml) of n-butyllithium (0.067 mol) over about 10 minutes at a liquid temperature kept at 20° to 25° C. After completion of the addition, the mixture was kept at 25° C. for 30 minutes, and then cooled to 5° C., followed by dropwise adding 4-propylcyclohexanone (11.2 g, 0.08 mol) over 20 minutes while the temperature was kept at 5° to 10° C., further keeping the temperature at 45° C. for 30 minutes, dropwise adding water (20 ml), further dropwise adding 6N-HCl (40 ml) while the temperature was kept at 30° C. or lower, separating off the resulting organic layer, adding potassium hydrogen sulfate (KHSO$_4$) (2 g), distilling off the solvent on heating, concentrating until the liquid temperature reached 110° C., during which dehydration reaction proceeded, cooling, transferring into a separating funnel, washing the resulting organic layer with water, distilling off the solvent, recrystallizing the residue from ethyl alcohol (10 c.c.) to obtain trans-4-methyloxymethyl-1-(4'-methyl-1-cyclohexenylphenyl)-cyclohexane (VII) (5.3 g) having a melting point (C-S point) of 64° C., a S-N point of 93.4° C. and a clearing point (N-I point) of 14.3° C.

Sixth step

In a 300 ml three-neck flask were mixed together the compound (VII) (5.3 g, 0.016 mol) obtained at the fifth step, chloranil (9.2 g, 0.037 mol) and xylene (76 ml), followed by heating under reflux for 24 hours, cooling, filtering off insoluble solids, concentrating to remove xylene, and recrystallizing the resulting raw crystals from ethyl alcohol to obtain the objective purified compound, trans-4-methyloxymethyl-1-(4'-propylbiphenylyl-4)cyclohexane (0.5 g), which had a melting point (C-N point) of 122.4° C. and a clearing point (N-I point) of 157.1° C. The elemental analysis values accorded well with calculated values as follows:

|   | Observed values (%) | Calculated values (%) (in terms of $C_{23}H_{30}O$) |
|---|---|---|
| C | 85.62 | 85.66 |
| H | 9.30  | 9.38 |

EXAMPLES 2~4

Example 1 was repeated except that methyl alcohol was replaced by ethyl alcohol (Example 2) or propyl alcohol (Examples 3 and 4) at the third step of Example 1, and also 4-propylcyclohexanone was replaced by 4-methylcyclohexanone (Example 2), 4-ethylcyclohexanone (Example 3) or 4-butylcyclohexanone (Example 4) at the fifth step of Example 1, to obtain compounds of Examples 2~4 listed in Table 1. The values of their physical properties are shown in Table 1 together with the results of Example 1.

TABLE 1

| Example | In Formula (I) $R_1$ | In Formula (I) $R_2$ | C-N point | C-S point | S-N point | N-I point |
|---|---|---|---|---|---|---|
| 1 | CH$_3$ | C$_3$H$_7$ | 122.4 | — | — | 157.1 |
| 2 | C$_2$H$_5$ | CH$_3$ | 90.7 | — | — | 139.5 |
| 3 | C$_3$H$_7$ | C$_2$H$_5$ | — | room temp. or lower | 115.6 | 124.2 |
| 4 | C$_3$H$_7$ | C$_4$H$_9$ | — | room temperature or lower | — | 125.1 (S-I) |

EXAMPLE 5

Preparation of trans-4-methyloxymethyl-1-[4'-(trans-4-propylcyclohexyl)biphenyl-4]-cyclohexanone (a compound of the formula (I) wherein n=1, $R_1$=CH$_3$ and $R_2$=C$_3$H$_7$)

First step to fifth step

Into a 500 ml three-neck flask were placed compound (VI) (27.7 g, 0.084 mol) prepared in the same manner as the first step to the fourth step in Example 1 and dry toluene (60 ml), followed by dissolving at 20° C. with stirring. To the solution was dropwise added a commercially available 1.67N hexane solution (6.3 ml) of n-butyllithium (0.100 mol) over about 10 minutes while the liquid temperature was kept at 20° to 25° C., followed by keeping the temperature at 25° C. for 30 minutes, cooling to 5° C., dropwise adding a solution obtained by dissolving 4-(trans-4-propylcyclohexyl)cyclohexanone (19.5 g, 0.088 mol) in dry toluene (30 ml), through a dropping funnel so that the inner temperature could not exceed 10° C., keeping the temperature at 45° C. for 30 minutes, cooling, adding water (30 ml) and 6N-hydrochloric acid (60 ml), separating the resulting layers, adding potassium hydrogen sulfate (KHSO$_4$) (3 g) to the organic layer, distilling off the solvent by heating, concentrating until the liquid temperature reached 110° C., during which dehydration reaction proceeded, cooling, transferring into a separating funnel, washing the organic layer three times with water, distilling off the solvent, and recrystallizing the residue from ethyl acetate (20 ml) in a refrigerator to obtain a compound (VII) (15 g), which had a C-S point of 208.0° C., a S-N point of 234.1° C. and a N-I point of 280° C. or higher.

Sixth step

In a 200 ml three-neck flask were placed the above compound (VII) (4.8 g, 0.012 mol), chloranil (6.7 g, 0.027 mol) and xylene (60 ml), followed by refluxing for 24 hours, cooling, filtering off the resulting insoluble crystals, distilling off xylene, recrystallizing the resulting raw crystals from ethyl acetate (10 ml), filtering off and drying to obtain the objective trans-4-methyloxymethyl-1-[4'-(trans-4-propylcyclohexyl)biphenylyl-4]cyclohexane (1.3 g), which had a C-S point of 143.5° C., a S-N point of 196.1° C. and a N-I point of 280° C. or higher. The elemental analysis values of this product accorded well with the calculated values as follows:

|   | Observed value (%) | Calculated value (%) (in terms of $C_{29}H_{40}O_1$) |
|---|---|---|
| C | 86.03 | 86.08 |
| H | 9.94  | 9.97 |

EXAMPLES 6 AND 7

Example 1 was repeated except that methyl alcohol was replaced by ethyl alcohol or propyl alcohol at the third step of Example 1 to obtain the corresponding sodium alkoxide which were then reacted with p-toluenesulfonic acid and trans-4-phenylcyclohexyl methyl ester as in Example 1, followed by collecting fractions of 112°~115° C./1.5 mmHg and 127°~130° C./1.5 mmHg to obtain trans-4-ethyloxymethyl-1-phenylcyclohexane or trans-4-propyloxymethyl-1-phenylcyclohexane, whereby trans-4-ethyloxymethyl-1-[4'-

(trans-4-propylcyclohexyl)biphenylyl-4]cyclohexane (C-S point, 98.1° C.; S-N point, 202.6° C.; N-I point, 280° C. or higher) or trans-4-propyloxymethyl-1-[4'-(trans-4-propylcyclohexyl)biphenylyl-4]cyclohexane (C-S point, 74° C.; S-N point, 228° C.; N-I point, 280° C. or higher) was prepared.

EXAMPLE 8

(Use example 1)

A liquid crystal composition consisting of

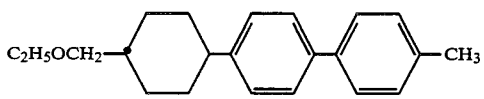

25.5 parts by weight 34.0 parts by weight, and 25.5 parts by weight, had a nematic liquid crystal temperature range (MR) of −3° to 52.5° C., a viscosity at 20° C., $\eta_{20}$ of 23 cp, a dielectric constant anisotropy $\Delta\epsilon$ of 11.3 ($\epsilon_\parallel$ = 16.2 and $\epsilon_\perp$ = 4.9) and a refractive index anisotropy $\Delta n$ = 0.120, and when it was sealed in a TN cell of 10 μm thickness, the resulting threshold voltage and saturation voltage were 1.50 V and 2.20 V, respectively.

To this composition was added a compound of Example 2,

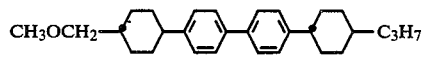

as one of the compounds of the present invention (15 parts by weight) to obtain a liquid crystal composition which had a MR of −3° to 60.7° C., that is, its N-I point was raised, and also had a $\eta_{20}$ of 24.8 cp, a $\Delta\epsilon$ of 10.2 ($\epsilon_\parallel$ = 14.7 and $\epsilon_\perp$ = 4.5), and a $\Delta n$ of 0.128, and when it was sealed in the same cell as above, the threshold voltage and saturation voltage were 1.66 V and 2.26 V, respectively.

EXAMPLE 9

(Use example 2)

A liquid crystal composition consisting of

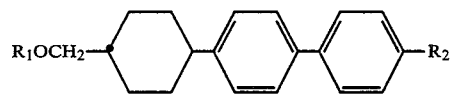

28.57 parts by weight 38.09 parts by weight, and 28.57 parts by weight, had a nematic liquid crystal temperature range (MR) of −3° to 52.5° C., a viscosity at 20° C., $\eta_{20}$ of 23 cp, and a dielectric constant anisotropy $\Delta\epsilon$ of 11.3 ($\epsilon_\parallel$ = 16.2 and $\epsilon_\perp$ = 4.9), and when it was sealed in a TN cell of 10 μm thickness, the resulting threshold voltage and saturation voltage were 1.5 V and 2.2 V, respectively.

To this composition was added a compound as one of the compounds of the present invention (4.76 parts by weight) to obtain a liquid crystal composition which had a MR broadened to −3° to 61.0° C., a $\eta_{20}$ of 25 cp, and a $\Delta\epsilon$ of 10.8 ($\epsilon_\parallel$ = 15.3 and $\epsilon_\perp$ = 4.5) and when it was sealed in the same cell as above, the threshold voltage and saturation voltage were 1.62 V and 2.30 V, respectively.

What is claimed is:

1. A trans-4-alkyloxymethyl-1-(4'-substituted biphenylyl-4)cyclohexane expressed by the formula wherein $R_1$ and $R_2$ each represent an alkyl group of 1 to 8 carbon atoms.

2. A compound of claim 1, wherein $R_1$ and $R_2$ each represent an alkyl group of 1 to 5 carbon atoms.

3. A liquid crystal composition comprising a mixture of compounds at least one of which is a compound of claim 1.

* * * * *